US012728103B2

(12) United States Patent
Skiba et al.

(10) Patent No.: US 12,728,103 B2
(45) Date of Patent: Sep. 8, 2026

(54) PHARMACEUTICAL COMPOSITION COMPRISING MITOTANE ADMINISTERED ORALLY FOR TREATMENT OF ADRENOCORTICAL CARCINOMA AND CUSHING'S SYNDROME

(71) Applicant: Mohamed Skiba, Montmain (FR)

(72) Inventors: Mohamed Skiba, Montmain (FR); Malika Lahiani-Skiba, Montmain (FR); Frédéric Bounoure, Bois Guillaume (FR); Michael Thomas, Mont-Saint-Aignan (FR); Hervé Lefebvre, N-D de Bondeville (FR)

( * ) Notice: Subject to any disclaimer, the term of this patent is extended or adjusted under 35 U.S.C. 154(b) by 816 days.

(21) Appl. No.: 17/639,578

(22) PCT Filed: Oct. 1, 2020

(86) PCT No.: PCT/IB2020/059218
§ 371 (c)(1),
(2) Date: Aug. 11, 2023

(87) PCT Pub. No.: WO2021/084345
PCT Pub. Date: May 6, 2021

(65) Prior Publication Data

US 2024/0058277 A1 Feb. 22, 2024

(30) Foreign Application Priority Data

Oct. 28, 2019 (FR) ...................................... 1912084

(51) Int. Cl.
*A61K 31/03* (2006.01)
*A61K 9/107* (2006.01)
*A61K 47/10* (2017.01)
*A61K 47/14* (2017.01)
*A61K 47/40* (2006.01)
*A61K 47/44* (2017.01)

(52) U.S. Cl.
CPC .............. *A61K 31/03* (2013.01); *A61K 9/107* (2013.01); *A61K 47/10* (2013.01); *A61K 47/14* (2013.01); *A61K 47/40* (2013.01); *A61K 47/44* (2013.01)

(58) Field of Classification Search
CPC ..................................................... A61K 31/03
USPC .......................................................... 514/750
See application file for complete search history.

(56) References Cited

U.S. PATENT DOCUMENTS 4,146,648 A 3/1979 Yabut
5,472,706 A 12/1995 Friedman et al.

FOREIGN PATENT DOCUMENTS

EP 2435022 B1 4/2012
WO 2012/071043 A1 5/2012

OTHER PUBLICATIONS

Alfonsi R. et al., "Characterization of mitotane (o,o '-DDD)—cyclodextrin inclusion complexes: Phase-solubility method and NMR," Annales Pharmaceutiques Francaises, vol. 71, Issue 3, pp. 186-192 (May 2013) (Year: 2013).*
Attivi D. et al., "Formulation et Pharmacocinetique De Systemes Autoemulsionnants De Mitotane (O,P'-DDD)," Internet Citation, pp. 1 (Jun. 15, 2008).

* cited by examiner

*Primary Examiner* — Raymond J Henley, III

(57) ABSTRACT

An object of the present invention is the preparation and use of a new dry emulsion (DE) containing mitotane and its use for the oral route for the treatment of adrenocortical carcinoma, congenital adrenal hyperplasia and Cushing's syndrome.

12 Claims, 2 Drawing Sheets

PHARMACEUTICAL COMPOSITION COMPRISING MITOTANE ADMINISTERED ORALLY FOR TREATMENT OF ADRENOCORTICAL CARCINOMA AND CUSHING'S SYNDROME

DESCRIPTION

Figure 1A:
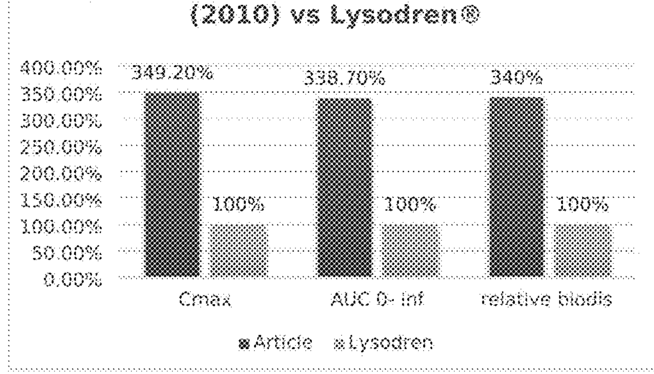
FIG. 1A depicts a comparison of pharmacokinetic parameters of a mitotane formulation versus Lysodren®, according to aspects of the present disclosure.

Adrenal cortex or adrenocortical carcinoma is a rare cancerous tumor that develops at the level of the adrenal cortex (Else T, et al., *Endocr Rev* 2014 35, 282-326; Fassnacht M, et al., *Nat Rev Endocrinol* 2011 7, 323-335). The annual incidence is estimated at 0.7 to 2 new cases per million inhabitants per year (Fassnacht M et al., J Clin Endocrinol Metab, 2013, 98:4551-4564), responsible for 0.04 to 0.2% of deaths due to cancer.

Adrenocortical carcinoma most often occurs in adults between 40 and 50 year old but also in children under 15 year old. This tumor is more often observed in women rather than men, without knowing the reason, but the prognosis of this disease is poor because it is diagnosed late and its medical treatment is very ineffective with a 5 year survival lower than 40% of cases (Assie G et al., J Clin Endocrinol Metab, 2007, 92:148-154). The total surgical excision of the tumor represents the best chance of total cure. An adjuvant treatment may be offered in addition to surgery. This consists in the oral administration of a derivative of the insecticide DDT, o',p'-DDD (ortho,para'dichloro-diphenyl-dichloroethane or mitotane) the only one approved for adrenocortical carcinoma of the formula chemical.

[Chem 1]

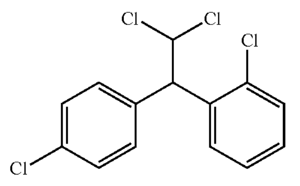

Chemical Structure of Mitotane

Similarly, in the inoperable advanced forms of the pathology, only mitotane is proposed because it remains to date the only drug with partial cytotoxic efficacy for the treatment of adrenocortical tumors. A pharmaceutical brand (Lysodren®) has been the subject of a European MA since 2004 and a MA in the USA since 1970 after the first clinical study carried out by the R. H. Moy team in 1960 (D M Bergenstal et al., Chemotherapy of adrenocortical cancer Vol 53,4, 1960), with official indications "the treatment of adrenal carcinoma in advanced forms in inoperable patients, in metastatic forms, or in recurrent forms" and as palliative treatment in the event of advanced disease.

Cushing's disease is caused by an adrenocorticotropic hormone (ACTH)-secreting pituitary tumor and is the most common cause of excessive endogenous cortisol secretion (Lacroix A, et al., Lancet. 2015; 386 (9996): 913-927. doi: 10.1016/S0140-6736 (14) 61375-1; Biller B M K, et al., J Clin Endocrinol Metab. 2008; 93 (7): 2454-2462. doi: 10.1210/jc.2007-2734; Pivonello R et al., Endocr Rev. 2015; 36(4):385-486. doi: 10.1210/er.2013-1048). Hypercortisolism can lead to significant morbidity and premature death compared to the general population (Pivonello R et al., Endocrinol Metab Clin N Am. 2008; 37 (1): 135-149. doi: 10.1016/j.ecl.2007.10.010). The primary goals for Cushing's disease treatment are to normalize the cortisol levels and reverse the signs and symptoms of hypercortisolism (Biller B M K, et al., J Clin Endocrinol Metab. 2008; 93 (7): 2454-2462. doi: 10.1210/jc.2007-2734; Pivonello R et al., Endocr Rev. 2015; 36(4):385-486. doi: 10.1210/er.2013-1048). The first-line treatment is transsphenoidal surgery (Biller B M K, et al., J Clin Endocrinol Metab. 2008; 93 (7): 2454-2462. doi: 10.1210/jc.2007-2734), although this is not always successful (Tritos N A et al., Nat Rev Endocrinol. 2011; 7 (5): 279-289. doi: 10.1038/nrendo.2011.12) and that patients could relapse several years after apparent surgical success (Dimopoulou C, et al., Eur J Endocrinol. 2013; 170 (2): 283-292. doi: 10.1530/EJE-13-0634).

A number of medical therapies are currently used in clinical practice for the treatment of Cushing's disease. These comprise mitotane (adrenolytic agent), pasireotide (analogue of somatostatin), cabergoline (dopamine receptor agonist), metyrapone and ketoconazole (inhibitors of adrenal steroidogenesis) and mifepristone (glucocorticoid receptor antagonist). Since not all patients with Cushing's disease derive sufficient benefit from available treatments, new formulations are always needed.

When Mitotane is administered in the form of a conventional tablet in humans, its oral bioavailability is poor with a value of 35 to 40% after 3 months of administration, that is to say that 60% of the product is found in the faeces in an unmetabolized form due to its very poor aqueous solubility (solubility: 1.29.10-7 mol/l at 25° C.) (Hahner S & Fassnacht M., Curr. Opinion. Investig. Drugs 2005 6 386-394; Igaz P. et al., Med Chem 2008 15 2734-2747).

To be effective, this active molecule must reach a plasma concentration of at least 14 mg/L (Terzolo M, et al., J Clin Endocrinol Metab 2000 85 2234-2238; Terzolo M, et al., Curr Opin Endocrinol Diabetes Obes 2014 21 159-165). This will only be achieved after an average of 3 months of treatment without therapeutic benefit for the patient during this period. This latency time is due at least in part to the fact that mitotane preferentially accumulates in fat at concentrations which could represent 200 times that of plasma, thus decreasing its bioavailability and its therapeutic efficacy. This accumulation in fat, combined with low bioavailability, makes it necessary to increase the doses administered to the patient to significant levels (10 to 15 tablets per day). Severe side effects have thus been identified, the most frequent of which are digestive disorders (nausea, vomiting and diarrhoea) directly related to the poor absorption of the molecule and neurological disorders (ataxia, depressive syndrome . . . ) when mitotaemia exceeds 20 mg/L. Recently, oral and vulvo-vaginal lichenoid reactions and encephalopathies have also been reported (Schmouchkovitch A. et al., Medicine (Baltimore) 2017; 96 (2): e5057; Betty Y. Lung et al., J. Clin oncol 33, 2015 (suppl: abst 4105); E. Pare et al., the oncologist 2017, 22:1-2).

The use of lipid formulations is one strategy for reformulating mitotane, like self-emulsifying systems (SESs) which are composed of surfactants, co-solvents and oils. These are not emulsions themselves, but under gentle stirring in the aqueous medium of the stomach, they form easily stable submicron-sized emulsions. These galenic forms have particular properties. They can modify the composition of the gastrointestinal contents, interact with membrane transporters and/or stimulate the transport of active ingredients by the lymphatic route. The absorption of these formulations, after oral administration, can take place through the lymphatic system which allows avoiding the hepatic first-pass effect. The lymphatic flow rate being slower than blood flow rate, this can prolong the absorption of the active ingredient (Singh et al., Crit Rev Ther Drug Carrier Syst, 2009, 26, 427-521).

Consequently, mitotane-based SESs offer the possibility of improving the oral bioavailability of mitotane, allow reducing the treatment time with a therapeutic benefit and limiting the number of tablets administered per day.

Thus, several pharmaceutical products of this type have appeared on the market, based on this formulation strategy with the administration of mean doses as with the brand Neoral® (cyclosporin A) and Kaletra® (lopinavir and ritonavir), or of lower doses as with the specialties Rocaltrol® (Calcitriol) and Avodart® (Dutasteride). But, to date, SESs have been marketed only in the form of soft capsules, which, although simple to make, have several drawbacks. Such as high manufacturing cost due to a low production rate, air entrapment in the capsule at high filling rates, and possible incompatibility of the SES components with the shell of the capsule which might reduce the service life of the product (Cole, E T; et al., *Adv. Drug Delivery. Rev.* 2008, 60, 747 to 756).

Three attempts have been made to solve the problems related to the formulation of self-emulsifying systems (SES) based on mitotane.

A first self-emulsifying system (SES) of mitotane has been developed by Attivi and collaborators (Attivi et al., Drug Dev Ind Pharm. 2010 April; 36(4):421-7), comprising mitotane dissolved in a matrix composed of an equal mixture of Capryol® 90, Tween®20 and Cremophor EL® (1/3:1/3:1/3).

Pharmacokinetic studies in rabbits have shown an improvement in bioavailability, multiplied by a factor of 3 compared to that of the Lysodren® specialty (Table 1) and [FIG. 1A].

TABLE 1

Pharmacokinetic parameters according to Attivi et al., (in rabbits)

| Parameters | units | Doses (100 mg/Kg) (n = 3) (Rabbits) Lysodren ® | SES (Attivi et al., 2012) |
|---|---|---|---|
| $C_{max}$ | mg/L | 0.63 | 2.2 |
| $T_{max}$ | H | 3.3 | 3.2 |
| $AUC_{0-\infty}$ | mg h/L | 3.1 | 10.5 |
| Relative bioavailability | | 1 | 3.4 |

The second, patent EP2435022 B1 relates to an invention which describes an SES of mitotane in the form of soft capsules which comprises mitotane dissolved in a matrix comprising:

propylene glycol monocaprylate;

propylene glycol dicaprate polyoxyethylene sorbitan monooleate

Figure 1B:
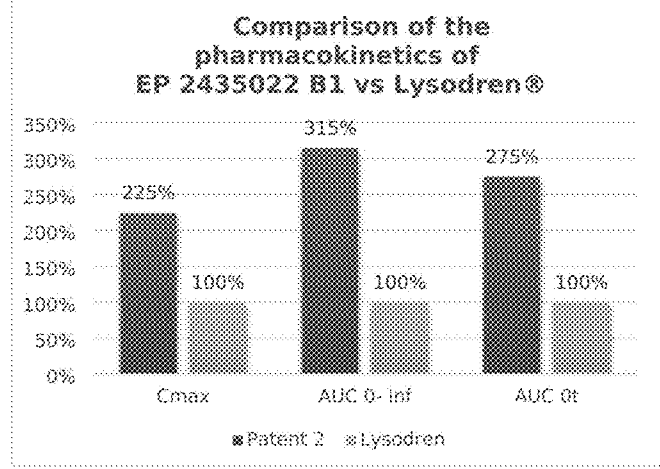
FIG. 1B depicts a comparison of pharmacokinetic parameters of another mitotane formulation versus Lysodren®, according to aspects of the present disclosure.

A bioavailability study conducted in dogs has also shown an improvement multiplied by a factor of 3 compared to that of the Lysodren® brand [FIG. 1B]. An improvement in bioavailability multiplied by a factor of 3 remains very low to reduce the 3-month therapeutic waiting period and to reduce the number of drug intakes per day.

And lastly, the Patent WO 2012/071043 A1, an invention that describes another formulation of mitotane based on the concept of SES with more than 70% of surfactants and in the form of a soft capsule.

No bioavailability study has been performed.

Hence, the challenge is to develop a new formulation of mitotane allowing obtaining a better bioavailability compared to SES in order to reduce the therapeutic waiting period which is undoubtedly the biggest problem of mitotane, the individual inter and intra variations of the plasma levels as well as the number of drug intakes per day.

The development of lipid systems in a solid dosage form (dry emulsion (DE)) is another formulation strategy which, besides improving the bioavailability, offers other advantages in comparison with liquid or semi-solid systems. Such systems involve the solidification of liquid lipids mainly into several units such as powders, granules, tablets, mini-tablets and pellets from this powder. Consequently, a dry emulsion (DE) combines the advantages of liquid SESs, such as for example increased bioavailability, efficiency and safety of use, with those of solid (powder) dosage forms, such as easy handling and administration, better patient compliance, high stability and repeatability, faster and easier production at a lower cost. More specifically, they offer the following advantages:

They reduce the risk of interactions of the excipients of the lipid system with the shell of the capsule, thus offering improved stability due to the reduction of the risk of chemical degradation and microbial growth and implying improved shelf life (Ma, H et al., *Chem. Pharma. Taureau.* 2014, 62, 1173-1179).

They can be administered as immediate or controlled release formulations depending on the choice of the powder excipient(s).

The dose is presented in the accurate weight of the dry emulsion powder, granules, mini-tablets or pellets filled into a capsule or made into tablets.

The production cost is considerably less compared to filling soft capsules since dry emulsions, granules and pellets have an excellent fluidity, allowing for rapid and repeatable filling of the capsules or compression dies with high production rates.

In particular, the granules, mini tablets or pellets of dry emulsion, as multi-particulate systems, offer therapeutic advantages, characteristic of these forms. They favor the reduction of the variation of gastric emptying time, the painless passage in the intestine and the low risk of releasing a high dose of active substance (dumping effect). All these factors lead to the minimization or elimination of the inter and intra variability of plasma levels (Abuhelwa Y A; et al., *AAPS J.* 2016, 18, 1322-1333).

A dry emulsion (DE) is a solid formulation, prepared by drying a liquid primary emulsion which contains a solid carrier in its aqueous phase and from which a continuous phase emulsion can be reconstituted after in vitro rehydration (Remon and Corveleyn, *Int J Pharm,* 1998, 166, 65-74) or in vivo during oral administration (Remon and Corveleyn, *Int J Pharm,* 1998, 173, 149-155).

Depending on the nature of the dispersed phase, there are two types of DEs: (i) oil-in-water (O/W), (ii) water-in-oil (W/O). In O/W type DEs, the oil droplets (their size can vary from one or several tens of micrometers to about ten nanometers depending on whether it is a macro-, micro- or nano-emulsion) are dispersed in a water-soluble matrix (Christensen et al., *Int J Pharm,* 2001, 212, 195-202). Before drying, the primary emulsions are prepared from:

an oily phase (10-20%, m/m):

1. medium-chain triglycerides (such as Miglyol®812 (Ahmed and Ahoul-Einien, Eur J Pharm Sci, 2007, 35, 219-225), Phosal®53, Labrafac®CC), long-chain triglyceride vegetable oils (soybean oil (Pedersen et al., *Int J Pharm,* 1998, 171, 251-270), corn, sesame (Ahmed and Ahoul-Einien, *Eur J Pharm Sci,* 2007, 35, 219-225), unsaturated polyglycosylated glycerides (Labrafil® M 1944 CS), polyglyceryl-6-di-oleate (Plurol® Oleique CC 497) (Christensen et al., *Int J Pharm,* 2001, 212, 187-194);

one or more surfactants (2-4%, m/m):

Sodium caseinates (Dollo et al., *Eur J Pharm Sci,* 2003, 19, 273-280), polyethylene glycol/polypropylene glycol block copolymer (Poloxamer® 188) (Christensen et al., *Int J Pharm,* 2001, 212, 187-194), polyoxyethylene sorbitan monooleate (Tween® 80) (Ahmed et al., *Eur J Pharm Sel,* 2008, 35, 219-225);

an aqueous phase (70-80%, m/m) which contains hydrophilic polymers (natural starches (Hansen et al., *Int J Pharm,* 2005, 293, 203-211) or modified polymers (Christensen et al., *Int J Pharm,* 2001, 212, 187-194), methylcellulose Methocel® E15LV (Remon and Corveleyn, *Int J Pharm,* 1998, 166, 65-74) or sugars (5-30%, m/m) (maltodextrins (Jang et al., *Eur J Pharm Sel,* 2006, 28,405-411), lactose (Yin et al., *J Control Release,* 2009,140, 86-94), trehalose, mannitol (Hansen et al., *Int J Pharm,* 2004, 287, 55-66) and saccharose (Christensen et al., *Eur J Pharm Biopharm,* 2002, 53, 147-153).

Dry emulsions are also obtained by removing free water from a primary oil-in-water emulsion, by spray drying (Zhang et al., *Int J Pharm,* 2011,414,186-192), by lyophilization (Ahmed et al., *Eur J Pharm Sci,* 2008, 35, 219-225) or by evaporation of the aqueous phase under vacuum (Zhang et al., *Int J Pharm,* 2011, 415, 293-300). Spray and lyophilization drying processes are the most widely used. The powder thus obtained can either be used directly as it is to fill capsules, or undergo treatments, such as, for example, a step of wet granulation in a non-aqueous medium, compaction or still compression ending with tablets (Hansen et al., *Int J Pharm,* 2005, 293,203-211). When the emulsion is rehydrated, the oil droplets are released to form an oil-in-water emulsion again.

However, the formulation of DEs is not simple to implement; drying remains a very critical step. The lyophilization is a long, complex, demanding and expensive (investment and energy consumption) process. Hence, DEs have some drawbacks: the powders obtained after drying of the emulsions are generally bulky, cohesive, with poor flowability, hygroscopic, which makes them difficult to handle without additional treatment (Christensen et al., *Int J Pharm,* 2001, 212, 195-202).

An object of the invention is the preparation and use of a new formulation of mitotane in the form of a dry emulsion (powder) and its use for the oral route.

Quite surprisingly, the inventor has discovered a manufacturing method for obtaining a dry emulsion containing mitotane while avoiding the elimination of the liquid phase contained in the primary emulsion by adsorption, lyophilization or atomization.

The works of the inventors have shown that it is possible to formulate a new formulation of mitotane in the form of a dry emulsion (MDE), composed of oily substances, the oily phase is a vegetable oil or mixtures thereof, an animal oil or mixtures thereof, and/or a marine oil or mixtures thereof is present at a content lower than 50% by weight and of cyclodextrins. The pharmaceutical and veterinary composition comprising a mitotane dry emulsion formulation, this new formulation of mitotane can be used as is or to fill capsules, sachets or sticks but also, with or without granulation step(s), it can be compressed to make tablets by compression, and allowing obtaining pellets by spheronization extrusion.

Hence, the invention aims at providing a new formulation of mitotane in the form of a dry emulsion (MDE), in the form of a powder dispersible in water or in biological media, without surfactants and without organic solvents, and based on cyclodextrins selected from α-cyclodextrin, β-cyclodextrin and γ-cyclodextrin and in that the cyclodextrin derivatives are selected from hydroxypropylated, methylated, ethylated, sulphobutyl ether or acetylated derivatives of α-cyclodextrin, β-cyclodextrin and γ-cyclodextrin and the binary or ternary mixtures of said cyclodextrins and of said cyclodextrin derivatives, and is present at a content higher than 45% by weight to avoid the phenomena of recrystallization and precipitation of mitotane.

The mitotane dry emulsions (MDE) according to the invention are characterized in that they are produced from oily substances loaded with mitotane with or without a co-solvent, thus with or without absorption promoters which are selected, for example, from the following compounds: glyceryl caprylate/caprate, Macrogolglycerol hydroxystearate, Macrogolglycerol ricinoleate (Cremophor EL®), polyoxyethylene sorbitan oleate, diethylene glycol monoethyl ether, propylene glycol monocaprylate, absolute ethanol, and macrogol 800 to 300, and which are present at a content from 10 to 20% by weight and of cyclodextrins or mixture thereof, and form after addition of an aqueous phase a water-in-oil (W/O) primary emulsion, an essentially solid set in a powder form.

A method of preparing the dry mitotane emulsion suitable for forming a mitotane delivery system, which comprises the solubilization of mitotane in an oil phase with or without a co-solvent, the addition of cyclodextrin in the oil phase with or without absorption promoter, the addition of the aqueous phase to obtain an O/W primary emulsion then a dry emulsion based on mitotane, drying and grading of the grains containing proportions of oil, cyclodextrin and mitotane lower than 50%, lower than 60% and higher than 6% respectively.

Example 1: Preparation of a W/O Dry Emulsion Containing Mitotane (MDE)

In one step, 25 ml of corn oil mixture loaded with 5 grams of mitotane and 3 ml of ethanol as a co-solvent are introduced into a planetary mixer (Hobart type) to improve the solubility of the mitotane in the oil phase. 42.5 grams of α-cyclodextrins dispersed in the oily phase are added under stirring (variator No. 1) and at room temperature (25° C.). The W/O mitotane dry emulsion is formed after adding an aqueous phase (5 ml of water) under stirring (variator No. 2). The wet granules are then calibrated (1 μm mesh) in an oscillating granulator, then dried in an oven at 45° C. for 15 minutes until a moisture content of 5 to 6% and elimination of alcohol. Granules with an average size of 800 μm loaded with 6.8% of mitotane are obtained.

Example 2: Preparation of a W/O Dry Emulsion Containing Mitotane (MDE) with Absorption Promoter Operation is carried out as described in Example 1, but using 10 to 20% of cremophore EL® or polysorbate 80 as mitotane absorption promoter. Granules with an average size of 800 μm loaded with 6.8% mitotane are obtained.

Example 3: Preparation and Biopharmaceutical Assessment of a W/O Dry Emulsion Containing Mitotane (MDE)

Preclinical Study

Oral administration of mitotane in the form of a dry emulsion (MDE) prepared according to Example 1 has been assessed in six rats (Charles River®) with an average weight of 350 g. The dosage administered orally is 100 mg/kg for the innovative formula and has been compared to the Lysodren® specialty (marketed reference drug). The samples have been taken at regular times: 0, 1H, 2H, 3H, 4H, 5H, 7H and 9H. The plasma dosage of mitotane is carried out using a blood sample taken on a dry, heparinized tube. Those samples are centrifuged and the supernatant is stored in a glass hemolysis tube at a temperature of −20° C. The plasma is purified by precipitation with methanol. Chromatographic analysis (HPLC) uses a LiChrospher 100®$C_8$ column, 5 μm in diameter and thermostated at 40° C., with an isocratic mobile phase, composed of a mixture of acetonitrile and acetic buffer pH 3.2 (75:25). The flow rate is 1.2 mL/min. Mitotane is detected at a wavelength of 234 nm. The retention time is 6 min for a sample analysis time of 9 min.

Figure 2:
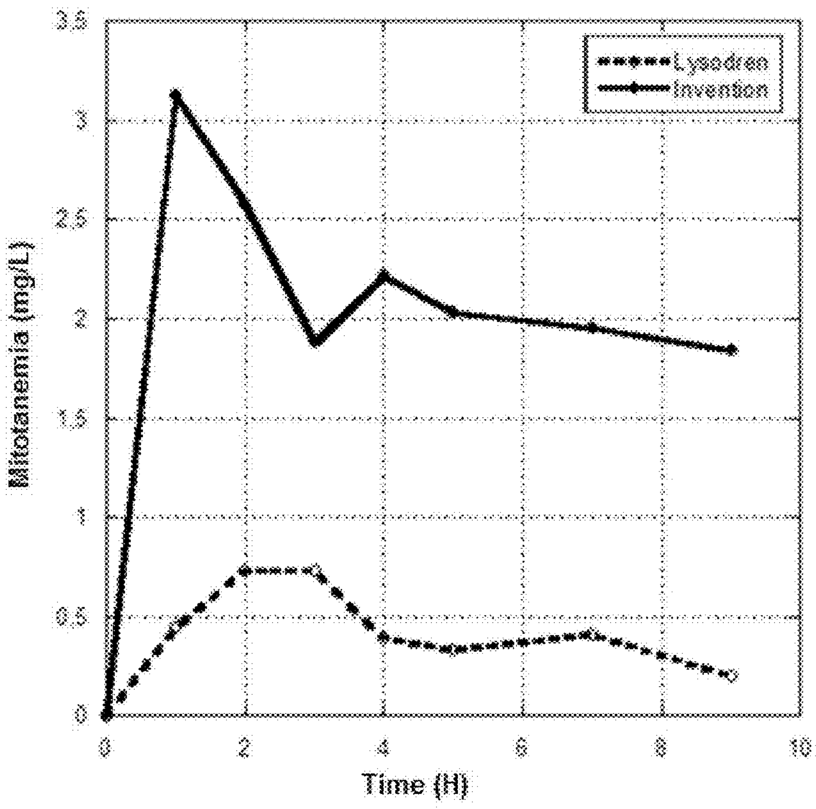
FIG. 2 depicts a comparison of pharmacokinetic profile of dry emulsion versus Lysodren®, according to aspects of the present disclosure.

The plasma concentrations of mitotane in dry emulsion form (MDE) (according to the invention), compared with those of the reference specialty Lysodren®, are represented in Table 2 and [FIG. 2].

TABLE 2

Pharmacokinetic parameters of the invention (in rats)

| Parameters | units | Doses (100 mg/Kg) (n = 3) (Rats) | |
|---|---|---|---|
| | | Lysodren ® | Dry emulsion (invention) |
| $C_{max}$ | mg/L | 0.7 | 3.1 |
| $T_{max}$ | H | 2 | 1 |
| $t_{1/2}$ | H | 1.930 | 23.866 |
| $AUC_{0-\infty}$ | mg h/L | 4.4 | 81.9 |
| $AUMC_{\infty}$ | mg h*h/L | 22.2 | 2834.4 |
| $MRT_{0-\infty}$ | H | 5.1 | 34.6 |
| Vd | L | 63.9 | 42 |
| CL | L/H | 21.768 | 1.176 |
| $t_{1/2}$ (de Vd & CL) | H | 1.9 | 23.9 |
| Relative bioavailability | | 1 | 18.61 |

The obtained main results are as follows:

The area under the curve (AUC) has been multiplied by a factor of 28 compared to that of Lysodren®

The maximum time ($T_{max}$) has been reduced by half compared to that of Lysodren®.

Figure 1C:
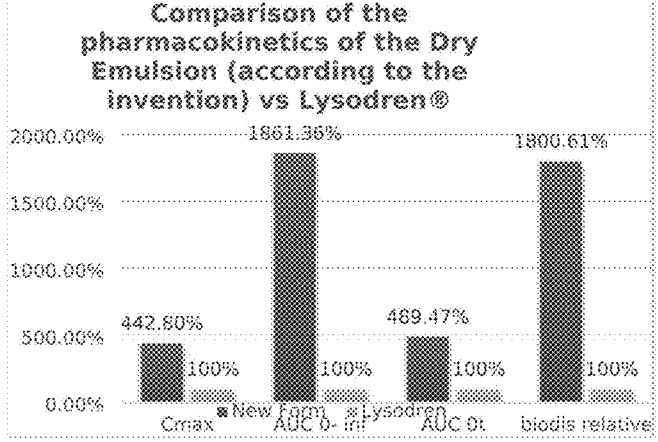
FIG. 1C depicts a comparison of pharmacokinetic parameters of a dry emulsion formulation versus Lysodren®, according to aspects of the present disclosure.

An analysis of the results between the mitotane dry emulsion (MDE), the published works according to D. Attivi (Attivi et al., Drug Dev Ind Pharm. 2010 April; 36(4):421-7), and the patent EP2435022 B1 compared to the Lysodren® specialty is presented in [FIG. 1]:

As regards the AUC 0-inf: the self-emulsifying system (SES) of mitotane developed by Attivi (Attivi et al., Drug Dev Ind Pharm. 2010 April; 36(4):421-7) shows an improvement multiplied by a factor close to 3.4, the patent EP 2435022 allows the improvement by a factor of 3.15 and the present invention allows obtaining an AUC 0-inf multiplied by a factor close to 19.

As regards the AUC 0t: the self-emulsifying system (SES) of mitotane developed according to the patent EP 2435022 shows an improvement multiplied by a factor of 2.75 and the present invention allows obtaining an AUC 0-inf multiplied by a factor close to 4.9.

As regards the relative bioavailability: the self-emulsifying system (SES) of mitotane developed by Attivi et al., shows an improvement multiplied by a factor of 3.4 and the present invention allows obtaining a relative bioavailability multiplied by a factor of 18.

As regards the Cmax: the self-emulsifying system (SES) of mitotane developed by Attivi et al., shows an improvement multiplied by a factor of 3.5, the patent EP 2435022 allows the improvement by a factor of 2.2 and the present invention allows obtaining a Cmax multiplied by a factor close to 4.5.

The invention claimed is:

1. A formulation of mitotane dry emulsion comprising:
an oily phase enriched with mitotane and cyclodextrin containing, or not, a co-solvent and/or an absorption promoter.

2. The formulation according to claim 1, wherein the oily phase is a vegetable oil or mixtures thereof, an animal oil or mixtures thereof, and/or a marine oil or mixtures thereof that is present at a content lower than 50 weight %.

3. The formulation according to claim 1, wherein the oily phase comprises absorption promoters and/or co-solvents which are:
selected from the following compounds:
glyceryl caprylate/caprate,
macrogolglycerol hydroxystearate,
macrogolglycerol ricinoleate (Cremophor EL®),
polyoxyethylene sorbitan oleate,
diethylene glycol monoethyl ether,
propylene glycol monocaprylate,
absolute ethanol, and
macrogol 800 to 300, and
present at a content of 10 to 20 weight %.

4. A pharmaceutical and veterinary composition comprising a dry emulsion formulation of mitotane as defined in claim 1.

5. The composition according to claim 4, in a form suitable for oral administration.

6. A formulation in the form of soft capsules or hard capsules containing mitotane in an oil phase and cyclodextrin, as defined in claim 1.

7. A pharmaceutical and veterinary composition comprising a dry emulsion formulation of mitotane as defined in claim 2.

8. The composition according to claim 7, in a form suitable for oral administration.

9. A pharmaceutical and veterinary composition comprising a dry emulsion formulation of mitotane as defined in claim 3.

10. The composition according to claim 9, in a form suitable for oral administration.

11. A formulation in the form of soft capsules or hard capsules containing mitotane in an oil phase and cyclodextrin, as defined in claim 2.

12. A formulation in the form of soft capsules or hard capsules containing mitotane in an oil phase and cyclodextrin, as defined in claim 3.

* * * * *